United States Patent
Cyr et al.

(10) Patent No.: US 7,050,660 B2
(45) Date of Patent: May 23, 2006

(54) MICROFLUIDIC DETECTION DEVICE HAVING REDUCED DISPERSION AND METHOD FOR MAKING SAME

(75) Inventors: Douglas R. Cyr, Livermore, CA (US); Roger L. Farrow, Pleasanton, CA (US); Don W. Arnold, Livermore, CA (US)

(73) Assignee: Eksigent Technologies LLC, Dublin, CA (US)

( * ) Notice: Subject to any disclaimer, the term of this patent is extended or adjusted under 35 U.S.C. 154(b) by 33 days.

(21) Appl. No.: 10/410,313

(22) Filed: Apr. 7, 2003

(65) Prior Publication Data

US 2004/0197043 A1  Oct. 7, 2004

(51) Int. Cl.
*G02B 6/00* (2006.01)

(52) U.S. Cl. .......................................... 385/12; 356/248
(58) Field of Classification Search ................... 385/12; 356/246
See application file for complete search history.

(56) References Cited

U.S. PATENT DOCUMENTS

| | | | | |
|---|---|---|---|---|
| 4,823,168 | A | * | 4/1989 | Kamahori et al. ........... 356/246 |
| 5,140,169 | A | * | 8/1992 | Evens et al. ................ 250/576 |
| 5,444,807 | A | | 8/1995 | Liu ............................ 385/125 |
| 5,570,447 | A | | 10/1996 | Liu ............................ 385/125 |
| 5,608,517 | A | | 3/1997 | Munk ......................... 356/246 |
| 5,757,482 | A | | 5/1998 | Fuchs et al. ................ 356/246 |
| 5,917,606 | A | | 6/1999 | Kaltenbach .................. 356/440 |
| 6,144,447 | A | * | 11/2000 | Ohman et al. .............. 356/246 |
| 6,188,813 | B1 | | 2/2001 | Dourdeville et al. .......... 385/12 |
| 6,224,830 | B1 | | 5/2001 | Harrison et al. .......... 422/82.11 |
| 6,542,231 | B1 | | 4/2003 | Garrett ....................... 356/246 |
| 6,678,051 | B1 | | 1/2004 | Gerner et al. ............... 356/456 |
| 6,867,857 | B1 | * | 3/2005 | Hobbs ........................ 356/246 |

(Continued)

OTHER PUBLICATIONS

Chervet, J.P. et al., *Anal. Chem.*, 68:1507-1512 (1996).

(Continued)

*Primary Examiner*—Juliana Kang
(74) *Attorney, Agent, or Firm*—Sheldon & Mak; Jeffrey G. Sheldon

(57) ABSTRACT

A microfluidic detection device provides reduced dispersion of axial concentration gradients in a flowing sample. The microfluidic detection device includes a cell body and a flow path through the cell body. The flow path has an inlet segment, an outlet segment, and a central segment, which forms a detection cell. The central segment is located between and at an angle with both the inlet segment and the outlet segment. The central segment has a first junction with the inlet segment and a second junction with the outlet segment. The cell body contains two arms that can transmit light to and from the detection cell. At least a portion of a first arm is located in the first junction and at least a portion of a second arm is located in the second junction. The portions of the arms located in the junctions are situated so that fluid entering or exiting the central segment of the flow path flows around the outer surface of one of the portions. By ensuring that the flow velocity is high near the walls both at the beginning and at the end of the conduit, the configuration serves to counteract dispersion caused by the normal parabolic velocity profile of flow through a cylindrical conduit, where the fluid velocity is highest at the center. In addition, the configuration promotes efficient sweeping of the entire volume between the two arms. A method for manufacturing the microfluidic detection device is also provided.

27 Claims, 3 Drawing Sheets

U.S. PATENT DOCUMENTS

2003/0076491 A1* 4/2003 Mueller et al. ............. 356/246
2004/0080744 A1* 4/2004 Hobbs ........................ 356/246

OTHER PUBLICATIONS

Goddard, N.J., et al., International Conference on Microtechnologies, *MicroTEC 2000*, pp. 25-27 (Sep. 2000, Hanover, Germany).

Grosse, A. et al., *J. Micromech. Microeng.* 11:257-262 (2001).

Malins, C. et al., *Analyst*, 126:1293-1297 (2001).

Vissers, J.P.C., *J. Chromatogr. A*, 856:117-143 (1999).

Wang, H., et al., *Analyst*, 125:1061-1064, (2000).

PCT International Search Report, PCT/US04/10234.

* cited by examiner

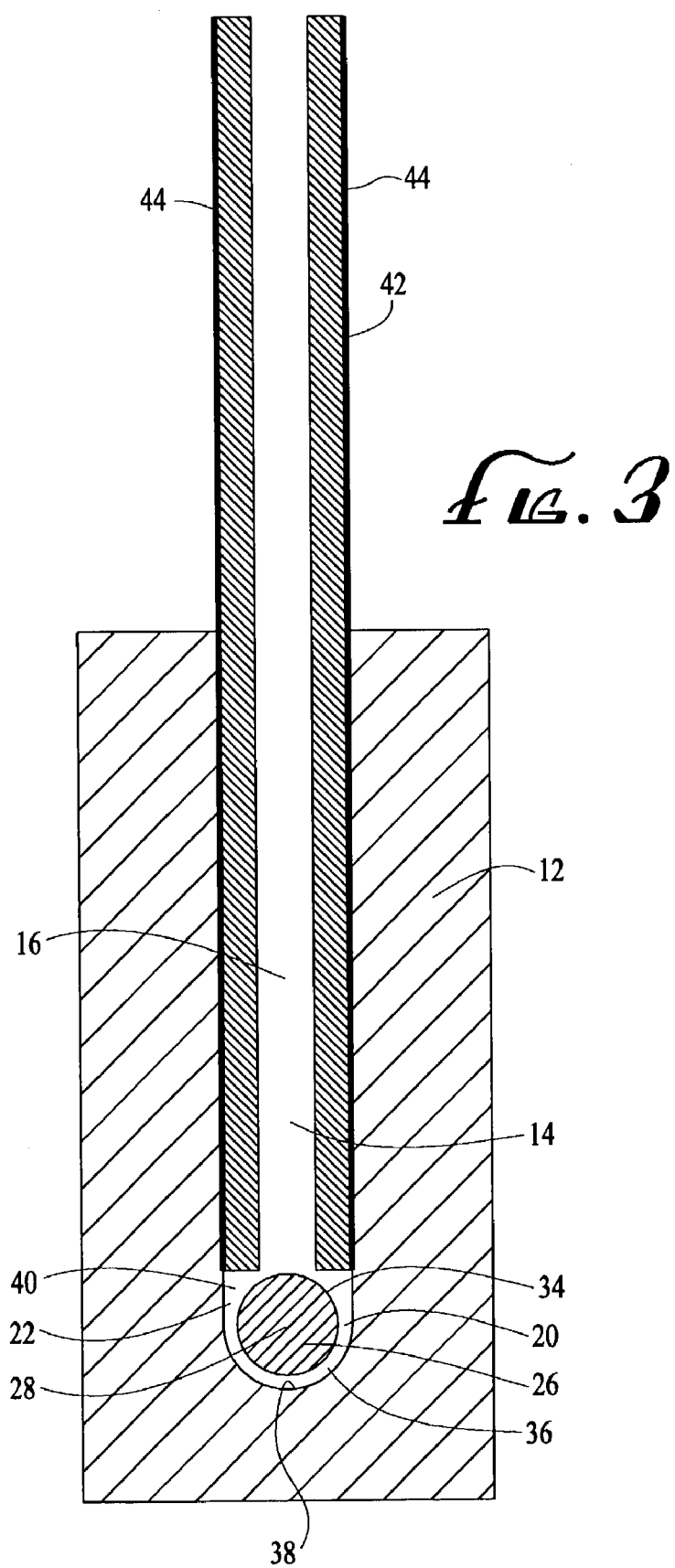

MICROFLUIDIC DETECTION DEVICE HAVING REDUCED DISPERSION AND METHOD FOR MAKING SAME

BACKGROUND

High performance liquid chromatography (HPLC) is a technique that has been used for many years as a means of separating, identifying, purifying and quantifying components of often-complex mixtures. HPLC is an important tool used by biotechnological, biomedical, and biochemical research as well as in the pharmaceutical, cosmetics, energy, food, and environmental industries.

Conventional HPLC typically is performed using chromatographic columns with inside diameters (I.D.'s) in the range of 2.0–4.6 mm, 4.6 mm columns being a common standard. However, microcolumn LC, which is the most widely accepted term to describe liquid chromatography using packed columns having inside diameters of 2.0 mm or less, is gaining in popularity. Advantages of microcolumn LC include the ability to analyze smaller sample volumes, reduction of solvent usage, and enhanced mass sensitivity.

A relevant scaling factor in the design of LC systems is the square of the ratio of the inner diameters of the columns. The flow rate, the injection volume and the detection volume, among other parameters, all need to be decreased in proportion to this factor when the column I.D. is reduced in order to maintain chromatographic resolution.

Optical detectors are often used in HPLC systems to detect separated analytes within a fluid mixture following elution through a chromatographic column. Consistent with the scaling factor mentioned above, the volumes of optical detectors developed for use in conventional HPLC systems are too large to yield useful data when used in microcolumn LC systems. Such detectors would fail to adequately resolve components with small separations.

Another quantity that must be reduced to preserve performance when the column I.D. is reduced is the overall dispersion caused by the chromatographic system. Dispersion results in band broadening and the concomitant loss of chromatographic resolution. Variance is the second moment of the distribution function of a chromatographic peak and is the statistical quantity used to quantify dispersion. In the case of normal distributions, variance is the square of the standard deviation. The total variance of a peak is the sum of the variances resulting from both columnar and extra-columnar, or instrumental (injector, transfer lines, detector, etc.) sources. To preserve the separation resolution achieved by the column as the column I.D. is reduced, the extra-column variance must decrease by the ratio of the column inner diameters raised to the fourth power. While the variance contribution from instrumental sources is constant during a chromatographic run under the same experimental conditions, the variance due to the column is proportional to the square of the elution time. For this reason, the contribution of instrumental variance to total variance will be largest at early elution times. An acceptable amount of variance due to instrumental dispersion is considered to be about 10% of the column variance at the elution time of a non-retained peak ($k=(t-t_{nr})/t_{nr}=0$, where k is the retention factor, t is the retention time of a given peak, and $t_{nr}$ is the retention time of a non-retained peak, which is the time it takes the mobile phase to flow from the injector, through the column, to the detector).

An example of the dramatic reduction in instrumental variance required to preserve the column efficiency in microscale HPLC systems can be derived by adapting information given in J. P. C. Vissers, "Recent Developments in Microcolumn Liquid Chromatography" J. Chromatogr. A 856 (1999) 117–143. Extrapolating from Vissers, the maximum acceptable variance due to instrumental dispersion (10% of the column variance) at k=0 for a column having a 1.0 mm inner diameter and a 15.0 cm length is 90,600 $nl^2$, whereas for a column having a 300 μm inner diameter, the maximum acceptable variance due to instrumental dispersion is about 740 $nl^2$ for equivalent experimental conditions.

Techniques known in the art, such as the "stacking" of analytes at the head of a column prior to gradient elution, can be used to minimize the contribution of instrumental variance from components prior to the column. However, contribution from instrumental sources following the column, notably the detection cell, cannot be reduced in this manner. Accordingly, there is a need in the art for a microfluidic detection device having reduced dispersion that can perform photometric measurements on a flowing liquid sample and which is suitable for use in microcolumn LC systems.

SUMMARY

The present invention provides a microfluidic detection device that satisfies this need. A microfluidic detection device having features of the invention comprises a cell body and a flow path through the cell body. The flow path comprises an inlet segment having a first longitudinal axis, an outlet segment having a second longitudinal axis, and a central segment, which forms a detection cell. The central segment has a third longitudinal axis and is located between and at an angle with both the inlet segment and the outlet segment. The central segment has a first junction with the inlet segment and a second junction with the outlet segment. The third longitudinal axis is transverse to both the first longitudinal axis and the second longitudinal axis. The cell body contains two arms that can transmit light to and from the detection cell. At least a portion of a first arm is located in the first junction. At least a portion of a second arm is located in the second junction. The portions of the arms located in the junctions are situated so that fluid entering or exiting the central segment of the flow path flows around the outer surfaces. By ensuring that the flow velocity is high near the walls both at the beginning and at the end of the conduit, the configuration serves to counteract the dispersion caused by the normal parabolic velocity profile of flow through a cylindrical conduit, where the fluid velocity is highest at the center. In addition, the configuration ensures that the entire volume between the two arms is swept efficiently, and that no "corners" or other significant volumes having a low flow velocity profile exist. Such regions can increase dispersion significantly since an analyte can radially diffuse into these regions, fall behind the bulk of the material forming the chromatographic peak, and then subsequently diffuse out, resulting in a "tail" on the peak.

The arms can be substantially cylindrical. The arms can be comprised of optical fibers. The central segment can be substantially perpendicular to both the inlet segment and the outlet segment. Both the inlet segment and the outlet segment can be comprised of capillaries having an inner diameter smaller than the inner diameter of the central segment.

A method embodying features of the present invention for making a microfluidic device comprises the steps of: coating a first surface of a first and a second fused silica wafer with a first layer of silicon; transferring a first microconduit pattern into the first silicon layer on each wafer; transferring the first microconduit pattern from the first silicon layer to the first surface of each wafer so that the first surface of each silica wafer has the first pattern; removing the first layer of silicon from each wafer; securing together the first surfaces of each wafer so that the patterns on the first surface form a flow path; inserting a portion of inserting a first optical fiber into the flow path; adhering the first optical fiber to the wafer, wherein a first annular region exists between an inner surface of the flow path and the portion of the first optical fiber; inserting a portion of a second optical fiber into the flow path; and adhering the second optical fiber to the wafers, wherein a second annular region exists between the inner surface of the flow path and the portion of the second optical fiber, wherein light exiting one optical fiber can travel through a portion of the flow path before entering the other optical fiber. The method can also comprise the steps of: filling the conduits with wax; dicing the bonded pair of wafers into multiple microfluidic devices; and removing the wax. The method can also comprise the step of inserting and adhering optical fibers and capillaries into conduits.

Thus, the present invention provides a microfluidic detection device having reduced dispersion that can perform photometric measurements of a flowing liquid sample and is suitable for use in microcolumn LC systems.

BRIEF DESCRIPTION OF THE DRAWINGS

These and other features, aspects and advantages of the present invention will become better understood with regard to the following description, appended claims, and accompanying drawings where:

FIG. 3 is a cross-sectional view of the microfluidic detection device of FIG. 1 taken on line 3—3 in FIG. 1.

DESCRIPTION

The present invention is directed to a microfluidic detection device having reduced dispersion that can perform photometric measurements of a flowing liquid sample and is suitable for use in microcolumn LC systems. A microfluidic detection device according to the present invention has a detection cell that is configured so that the fluid velocity is highest near the walls of the detection cell at the entrance and exit of the cell. This design at least partially counteracts the dispersion caused by the usual parabolic velocity profile of fluid flow through a cylindrical conduit, where the fluid velocity is highest at the center.

Figure 1:
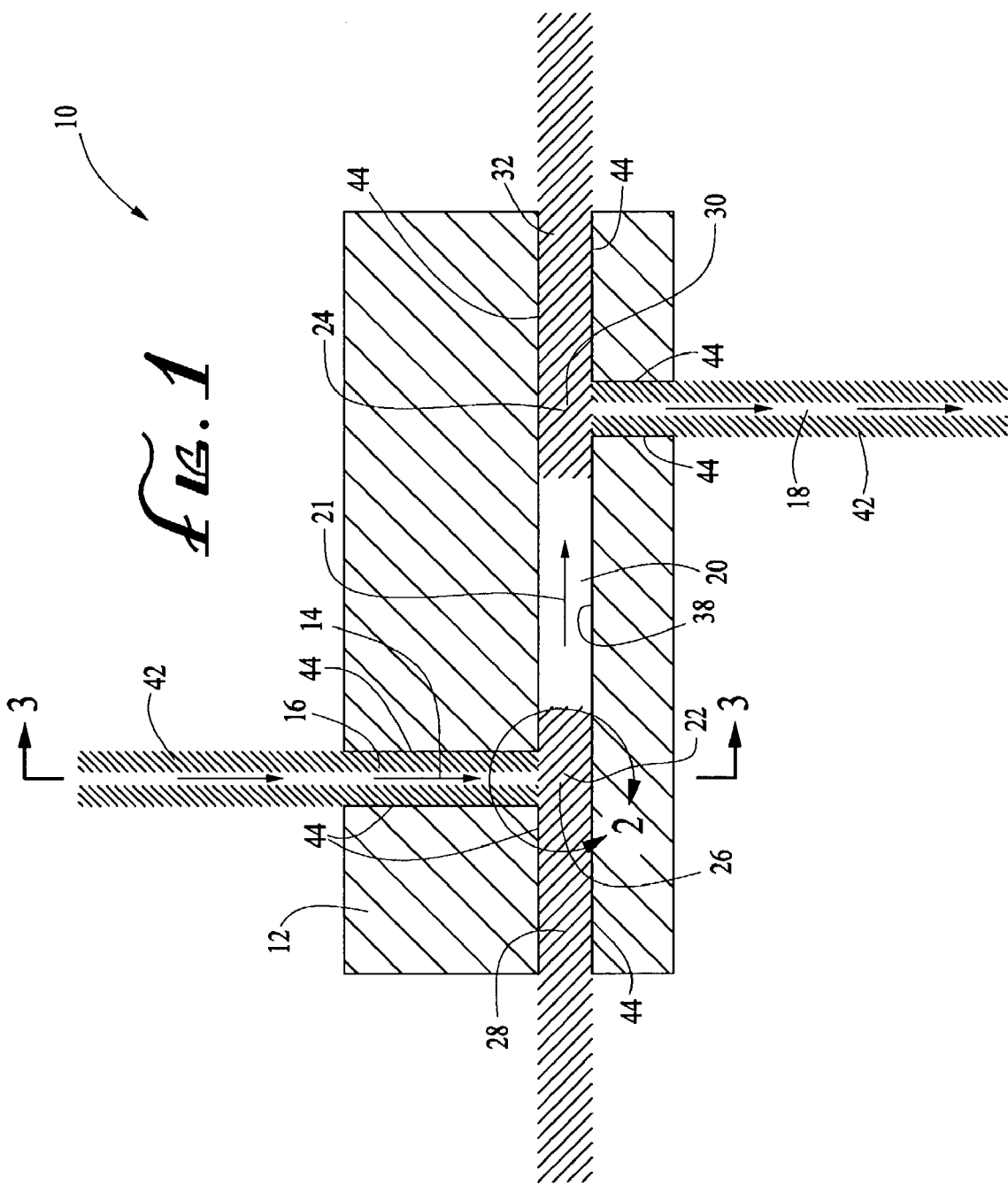
FIG. 1 is a cross-sectional view of one embodiment of a microfluidic detection device in accordance with the present invention.

A microfluidic detection device 10 according to the present invention is shown in FIG. 1 and includes a cell body 12 and a flow path 14 through the cell body. The flow path 14 has an inlet segment 16 having a first longitudinal axis, an outlet segment 18 having a second longitudinal a second longitudinal axis, and a central segment 20 having a third longitudinal axis and containing a detection cell 21 formed by the inner surface 38 of the central segment and the end faces of arms 28 and 32. The central segment 20 is located between both the inlet segment 16 and the outlet segment 18 and is in fluid communication with both the inlet segment and the outlet segment. The third longitudinal axis is transverse to both the first longitudinal axis and the second longitudinal axis, wherein "transverse" means at an angle other than 180°.

Figure 2:
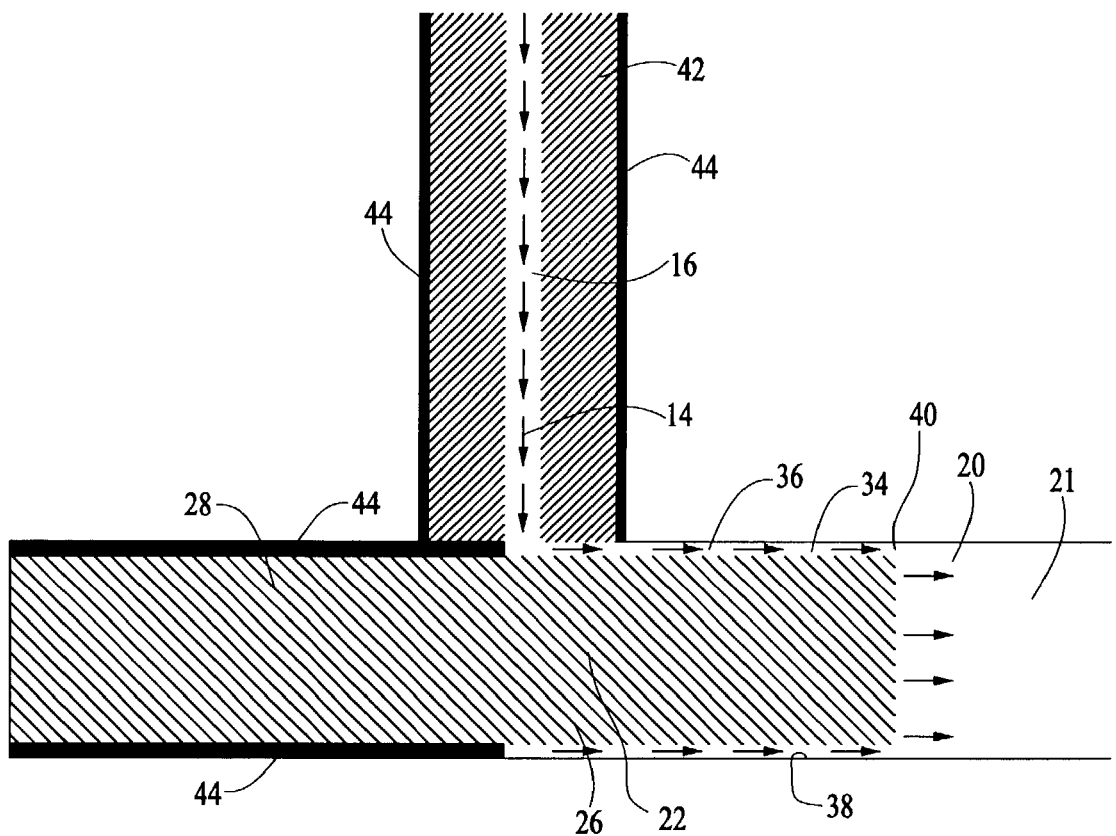
FIG. 2 is a detailed cross-sectional view of area 2 of the device of FIG. 1.

The central segment 20 has a first junction 22 with the inlet segment 16 and a second junction 24 with the outlet segment 18. At least a portion 26 of a first arm 28 is located in the first junction 22 and at least a portion 30 of a second arm 32 is located in the second junction 24. As can be seen best in FIGS. 2 and 3, the portions 26 and 30 of the arms 28 and 32 located in the junctions 22 and 24 are situated so that fluid entering or exiting the central segment 20 of the flow path 14 flows around the outer surface 34 of one of the portions 26 and 30, respectively. This causes the velocity of the fluid flowing through the central segment 20 to be more uniform than if the portions 26 and 30 of the arms 28 and 32 were not in the junctions 22 and 24. Hence, dispersion is reduced.

The arms 28 and 32 preferably are substantially cylindrical and have a substantially circular cross-section so that there are thin annular regions 36 between the outer surface 34 of the portions 26 and 30 and the inner surface 38 of the central segment 20. These annular regions 36 form annular openings 40 to the central segment 20. Fluid can flow in and out of the central segment 20, through the annular openings 40. The annular openings 40 ensure that the velocity of fluid flowing through the central segment 20 has a maximum near the walls both near the entrance and the exit of the central segment 20. Hence, dispersion is reduced.

It is desirable that the central segment 20 be configured so that there are no areas that are not swept by fluid, minimizing differences in flow velocities and, hence, dispersion. Preferably, except for the annular regions, the flow path 14 is substantially tubular, i.e. has a substantially circular cross-section, as the flow velocity profile is more uniform in a tubular flowpath as opposed to a flow path having a rectangular cross-section. In addition, the central segment 20 and the inlet segment 16 and outlet segment 18 are preferably formed in a "Z" configuration (rather than a "U" configuration) as shown in FIG. 1. In a "U" configuration (not shown), a flow streamline located near the cell wall adjacent to the inlet segment will have a shorter path to the outlet segment than will a streamline located near the opposite cell wall. The "Z" configuration will minimize dispersion caused by flow through the cell by subjecting the flow streams to equal but opposite pathlength differences upon exiting the central segment. This will help preserve the resolution of chromatographic peaks past the detection cell, in case they are routed elsewhere following optical detection.

In some embodiments including a bend in the flow path 14 prior to the first junction 22 can reduce dispersion further. This bend preferably is at an angle opposite (180° different than) that of the angle formed by the first and third longitudinal axis. For example, if the angle between the first and third longitudinal axis is −90°, the bend preferably forms an angle of approximately 90° in the flow path.

The portions 26 and 30 of the arms 28 and 32 in the junctions 22 and 24 can be end portions. The arms 28 and 32 can be comprised of any material that is capable of transmitting light of the wavelength used to analyze the fluid passing through the detection cell 21. In the preferred embodiment, each arm 28 and 32 is comprised of an optical fiber.

The angles formed by the intersection of the central segment 20 with the inlet segment 16 and the outlet segment 18 can be any angles between approximately 10 degrees and 170 degrees and need not be the same. However, if the fluid will be further analyzed after passing through the detection cell 21, it is preferable that the angles be substantially equal to each other so that dispersion resulting from passage through the flow cell is reduced.

The inner diameters of the inlet, outlet, and central segments 16, 18, and 20, respectively, need not be the same. In some embodiments, it is preferable that the inner diameter of the central segment 20 is larger than the inner diameters of the inlet and outlet segments 16 and 18, respectively, so that the inner diameter of the central segment is larger than an optical fiber, while the inlet and outlet segments 16 and 18, respectively, are comprised of standard, commercially available capillaries 42 that allow for easy connection to other microfluidic devices. A further reason that the inlet and outlet segments 16 and 18, respectively, have a smaller inner diameter than the central segment 20 in practice is that the inlet and outlet segments are initially etched to the same depth as the central segment and capillaries are glued within the inlet and outlet segments, effectively reducing their diameter. Therefore the effective diameter of the inlet and outlet segments when capillaries are used to connect the detection cell to other components within an analytical system are defined by the capillary inner diameter, rather than the etch depth of the conduit that they are adhered to. Further, the smaller inner diameter of the inlet and outlet segments 16 and 18, respectively, reduces the volume of the microfluidic detection device 10 while not reducing the cross-section of the detection cell 21. Reduction of the overall volume of the microfluidic detection device 10 minimizes dispersion.

It is important to note that flow through the annular region actually causes increased dispersion over that for a cylindrical tube having the same cross-sectional area. Therefore, even though a 2-um annulus around a ~110-um diameter fiber has approximately the same cross-sectional area as the 30 um diameter capillary, it has more dispersion. For this reason, it is preferable not to employ a longer annular region than necessary. Not using a longer annular region than necessary also helps to keep the backpressure of fluid flowing into the central segment at a lower level. It is preferable that the annular spacing, which is the space between the inner surface of the central segment and the arm, be no larger than necessary so that as much light as possible reaches the detector.

Annular openings in conjunction with a Teflon AF liquid waveguide flow cell are presented in U.S. Pat. No. 6,542,231. However, the patent teaches the use of a manifold or annular space prior to entering the waveguide in order to maintain laminar flow and avoid turbulence. While turbulence may be an issue in conventional HPLC systems, under microcolumn LC conditions the Reynolds number of the fluid never approaches the turbulent regime and therefore the flow is always laminar. The patent also gives no consideration to the optimum geometries (principally annular spacing and length) specified as part of the present invention to minimize dispersion for microcolumn LC applications, which are very sensitive to dispersion. For example, as mentioned above, flow through an annulus is actually more dispersive than through a conduit having an equivalent, circular, cross sectional area. Therefore, even if an annular region is incorporated into their flow cell design, there is no guarantee that dispersion will be minimized. In fact, it may be increased. In addition, possible methods of fabrication of the Teflon AF liquid waveguide flow cell described in the patent are not suited to achieving the close tolerances on very small dimensions required for the optimal performance of the present invention.

The best results are expected where the length of the annular region is approximately 1–40 times, more preferably approximately 4–10 times, the diameter of the arms or the optical fibers as measured from the from the centerline of either the inlet segment 16 or the outlet segment 18 to the face of the corresponding arm and the annular spacing is approximately 0.001 to 0.2 times, more preferably approximately 0.01–0.05 times, the diameter of the arms or the optical fibers. The annular spacing is the size of the annular region 36, which is the distance between the outer surface 34 of one of the arms 28 and 32 and the inner surface 38 of the central segment 20.

The cell body 12 can be comprised of a substrate such as silicon, silica, quartz, glass, or other ceramics. The cell body 12 can also be comprised of plastic or any other cell body material. The cell body 12 can be constructed using laser machining, embossing, molding, casting, micromachining methods, or any other construction method known in the art. Preferably, the cell body 12 is substantially transparent to certain wavelengths of light so that fluorescence, degenerate four wave mixing, Raman, refractive index, surface plasmon resonance, or other measurements can be taken through the cell body.

The detection cell volume used in microcolumn LC systems preferably is less than that of conventional systems in order to accurately analyze the smaller sample exiting the microcolumn. The factor by which conventional components preferably are reduced is equal to the ratio of the squares of the inner diameters of the chromatographic columns. This means that if one wants to use 300 µm I.D. columns rather that the conventional 4.6 mm I.D. columns, the volume of the detection cell 21 is preferably reduced by a factor of approximately 235.

However, to preserve the sensitivity of the detection cell, the pathlength over which the sample interacts with the light used in detection preferably remains close to the 1.0 cm pathlength of a conventional detection cell. Hence, the geometry of the detection cell 21 is preferably optimized to have cross sectional area large enough to allow sufficient light to propagate through the detection cell 21, but small enough to ensure that the pathlength can be maximized while the overall volume remains under the desired maximum value.

Light input to, and propagation through, this small detection volume can be accomplished, for example, by using an arm 28 or 32 comprised of an optical fiber to deliver light from a light source to one end of the detection cell 21. The light source can be a deuterium lamp, for example. The output of the deuterium lamp can be optimized and focused onto the end of one of the arms 28 or 32 using a lens system or ellipsoidal reflector, as just two examples of well-established techniques known in the art. Any technique can be used.

A light detector, such as a CCD array-based spectrometer, is used to detect light that passes through the flowing fluid sample and travels down the other arm. Any light source and detector known in the art and suitable for use with a microfluidic detection cell, as judged by one of ordinary skill in the art, can be used, including so-called single wavelength light sources and detectors, which actually supply or detect a narrow range of wavelengths.

In this way, the detection cell 21 can be constructed having both the required low volume and sufficient light throughput and pathlength. Since the detection device 10 is very small, the detection cell 21 can be located very close to other components in the system, a chromatographic column, for example, eliminating the need for long interconnecting conduits, which contribute to dispersion.

The microfluidic detection device 10 can be easily incorporated as a component within microfabricated, chip-based, full chromatographic separation systems in a compact and efficient manner.

Preferably, the microfluidic detection device 10 is manufactured using the steps detailed below, although any method known in the art can also be used, such as that described in A. Grosse, M. Grewe and H. Fouckhardt, "Deep Wet Etching of Fused Silica Glass for Hollow Capillary Optical Leaky Waveguides in Microfluidic Devices," J. Micromech. Microeng. 11, 257 (2001) and that described in U.S. patent Ser. No. 10/198,223 entitled Laminated Flow Device, invented by David W. Neyer, Phillip H. Paul and Jason E. Rehm, both of which are incorporated herein by reference for any and all purposes.

A pair of wafers are cleaned unless already clean. Standard wafer sizes can be used, 0.5–1 mm thickness, 100 mm diameter, as well as any desired size. The wafer can be made of silicon, glass, silica, quartz, or other ceramic materials. Further, when using silica, glass or quartz wafers, a first surface of the pair of wafers is coated with a first layer of silicon. The layer can have a thickness of 1000–3000 Angstroms, for example. The layer can be applied via low-pressure chemical vapor (LPCVD) deposition as is well known in the art. Amorphous silicon films are preferred related to other choices like photoresist, chrome, chrome/gold or titanium/platinum combinations for their reliability in defining channels in a fused silica substrate without edge defects that result from etchant-induced adhesion failure or pinholes in the film.

A first pattern for micro-conduits is transferred into the first layer of silicon on both silica wafers. The pattern can be transferred using standard lithography methods, like the one described in the following paragraph.

A lithography mask can be generated from a drawing of the desired micro-conduit pattern, typically by a commercial vendor using a chrome film (~1000 Angstrom thick) on a glass substrate. If one mask is used, the same mask can be used for both wafers in the pair. Preferably, a single mask can be used that contains a mirror plane of symmetry for those micro-conduits that that are desired to be approximately circular in cross-section. The micro-conduit pattern preferably is designed such that mirror-image alignment of the pattern on each wafer will contain micro-conduit traces that substantially overlap in regions of the fluidic manifold where cylindrical channels are desired. If two masks are used, one is used for each wafer in the pair. A thin film, 1–7 micrometers, for example, of photoresist (photosensitive polymer) is placed over the layer of amorphous silicon on the pair of silica wafers. The side of each silica wafer having the thin film of photoresist is placed proximal to or in contact with the mask. The desired microconduit pattern is transferred from the masks to the layers of photoresist by exposing the photoresist to UV light through the mask followed by appropriate development and curing of the photoresist. The microconduit pattern can be transferred from the photoresist to the silicon layer on each wafer by etching the exposed amorphous silicon with wet chemical etching, using a mixture of hydrofluoric, nitric, and acetic acid, for example, or dry chemical etching, using reactive ion etching with a low-pressure (~15-mTorr) plasma of a mixture of gases that includes $SF_6$, $C_2ClF_5$ and Ar, for example, or any other method known in the art.

After the first microconduit pattern is transferred into the first layer of silicon on both wafers, the first microconduit pattern is transferred into the first surface of the silica wafers so that each silica wafer has a patterned surface of conduits having a substantially semi-circular cross-section. This can be accomplished by wet chemical etching of the exposed regions of the silica. The wet chemical etching can be accomplished by timed submersion in a 49% solution of HF. Etch rates are typically on the order of 1.3 micrometers per minute for silica. As this etching process is isotropic, the microconduits that are formed in the wafers have a substantially semi-circular cross-section.

The photoresist can be removed using a mixture of sulfuric acid and hydrogen peroxide, for example. The first layer of silicon can be removed by dry or wet chemical etching, as described above.

Depending on the exact design, multiple etches can be used in the fabrication of the microfluidic detection device. For example, a first etch can be a shallow etch of about 1.5 microns and a second etch can be a deep etch of about 56 microns. Thus, the process is repeated using a second mask.

The shallow etch can be used to define the alignment marks on the wafers and any shallow structures that are to be incorporated into the design. The alignment marks are preferably shallow etched to provide improved alignment accuracy. In addition, the shallow etches can be used to provide regions of slightly larger diameter, i.e. 3 microns, when the regions that are shallow etched are subsequently deep etched.

The deep-etched regions are preferably etched approximately ½ the diameter of the capillaries and optical fibers to be inserted plus about 1–2 micrometers to allow a minimal space for adhesive between the capillaries and optical fibers and the walls of the microconduit. For example, semicircular conduits having a radius of 56 micrometers are etched to make conduits having a circular cross-section with a 112 micrometer diameter to accommodate capillaries and optical fibers having an outside diameter of 109 micrometers. Preferably, the wafers are thoroughly cleaned with acid and base cleaning solutions so that surfaces of the pair of wafers are hydrophilic. In addition, the wafers preferably are also megasonically cleaned so that the surfaces of the wafers are more hydrophilic.

The first surfaces of each wafer are secured together so that the patterns on the first surfaces form the flow path 14. The cleaned, patterned surfaces of the pair of silica wafers are substantially aligned and brought into contact so that the patterned surfaces form conduits having a substantially circular cross-section. The conduits can form the flow path 14 and a place to insert the arms 28 and 32 and, optionally other microfluidic components. Preferably, the alignment is accurate to within 3 micrometers. The patterned surfaces can be aligned using a commercially available wafer alignment device, such as the Electronic Visions EV520 aligner, which allows visual alignment of the two wafers while they are maintained co-planar with a very small separation by placing removable thin (40 microns) spacers between the wafers and avoiding contact of the two wafers prior to complete alignment through the adjustment of high precision positioning stages. With the alignment complete, the wafers are clamped with the spacers remaining between the wafers. A modest pressure (approximately 2–20 psi) is applied at the center of the wafers, normal to the plane of the wafers. At this point, a weak attachment between the wafers occurs as indicated by the visually observable bonding front that moves from the center to the edge of the wafer. As the bonding front forms, the spacers are removed so that the entire wafer finishes bonding.

The pair of wafers is heated so that they bond together permanently. Heating the wafers (to approximately 1165° C. for silica wafers) for about 4–8 hours is sufficient to drive a dehydration reaction at the interface of the two wafers resulting in an interfacial bonding of the two wafers. The exact bonding temperature is dependant on the materials of construction of the wafer. The result is a strong wafer bond in which the interface essentially disappears and the resultant part is a solid component in which microconduits of substantially circular cross section exist for the introduction of fluid, capillaries, optical fibers, electrical leads, etc.

After bonding, the conduits can be filled with wax or some other suitable sacrificial material to avoid particulate contamination of the microconduits when the wafers are diced into multiple microfluidic devices 10. A diamond saw can be used to dice the wafers. Removal of the wax can be accomplished by pyrolysis of the wax. 650° is a sufficient temperature for pyrolysis. Since the microfluidic devices can be very small, dicing a single pair of bonded silica wafers can yield a large number of microfluidic detection devices 10 and hence, the cost of manufacture of the devices can be lessened.

At this point, the resulting microfluidic devices 10 are ready for insertion and adhesion of fiber optic and fluidic-capillary components. The portions 26 and 30 of the arms 28 and 32 are inserted into the flow path 14. The arms are then adhered to the wafer so that annular regions 36 exist between the inner surface 38 of the central segment 20 and the portions 26 and 30 of the arms 28 and 32. The arms 28 and 32 are positioned so that light exiting the face of one arm can enter the face of the other arm after traveling through a portion of the flow path 14.

In the preferred embodiment of the microfluidic detection device 10, the bonded wafers form the cell body 12. A first arm 28, preferably an optical fiber, is inserted into a conduit that forms the central segment 20 so that at least a portion 26 of the first arm is located in the first junction 22. A second arm 32, preferably an optical fiber, is inserted into the central segment 20 so that at least a portion 30 of the second arm 32 is located in the second junction 24. Annular regions 36 exist between the inner surface 38 of the central segment 20 and the portions 26 and 30 of the arms 28 and 32. Capillaries 42 can be inserted into conduits in the cell body 12 to form the inlet and outlet segments 16 and 18, respectively. The capillaries 42 are not necessary although they are preferred for two reasons: 1) capillaries allow the microfluidic detection device to easily connect to other microfluidic devices and 2) the insertion of the capillaries makes the inner diameter of the inlet and outlet sections 16 and 18, respectively, smaller and the smaller inner diameter reduces the volume of the microfluidic detection device 10 while not reducing the cross-section of the detection cell 21.

The arms 28 and 32 and the capillaries 42 preferably are fixed to the cell body 12, via an adhesive 44. The adhesive 44 can be a UV activated optical cement or other type of glue, an inorganic seal, such as a solgel or an aerogel solution, or any other suitable adhesive known in the art. Alternatively the capillaries 42 and arms 28 and 32 can be directly fused to the cell body 12 using a $CO_2$ laser or any other appropriate directed heat source known in the art.

The arm and capillary connections are very robust since the area over which the adhesive 44 can act is large compared to the face of the arms 28 and 32 or capillaries 42. This allows high pressures to be applied to the system without causing the connections to fail. Microfluidic detection devices 10 manufactured in the manner described above have the capability to perform at pressures exceeding 5000 psi since the pair of silica wafers are directly bonded.

In operation, fluid that has just passed through a chromatographic column enters the inlet segment 16. The fluid flows through the inlet segment 16, the central segment 20, and the outlet segment 18. After exiting the outlet segment 18, the fluid may flow to waste. Alternatively the fluid may flow to other detection modules, such as the input to a mass spectrometer, or it may be selectively directed along different pathways using some sort of valving arrangement depending on information gleaned by the detector. For example, the output may be spotted onto MALDI (matrix-assisted laser desorption and ionization) plates only when analyte is confirmed to be present by the optical detector. As fluid flows through the central segment 20, light from a light source exits one arm 28 or 32 and passes through fluid. Much of the light not absorbed by the fluid enters the other arm 28 or 32, which preferably guides the light to a wavelength-dispersed linear array detector. However, depending on the length of the central segment 20, the light may have at least one occasion to reflect off of the wall. Since the index of refraction of the silica wall is higher than the fluid, conditions for total internal reflection are not satisfied. Rather, Fresnel reflection occurs, with a high probability of reflection, especially as the angle of incidence approaches 90 degrees. Nonetheless, the light has some probability of escaping the cell each time it must undergo a reflection. Some of the light will also back-reflect at the entrance surface of the second fiber (~2%). And lastly, FIG. 3 illustrates that it is possible for light to miss the entrance surface of the second fiber and be lost to the detector as it propagates down the annular region. This can be a significant fraction of the light, roughly equal to $((d_{20})^2-(d_{28})^2)/(d_{20})^2$ from geometric arguments, where $d_{28}$ is the diameter of the arms and $d_{20}$ is the diameter of the central segment. This is the main motivation for minimizing the annular spacing.

In an exemplary microfluidic detection device embodying the invention, semicircular conduits having a radius of approximately 57.5 μm were etched into wafers having a 1 mm thickness. The wafers were aligned and directly bonded as described herein to form circular conduits having a diameter of approximately 115 μm. The arms were optical fibers. Both the optical fibers and the conduits used had an outer diameter of approximately 110 μm. The inner diameter of the capillaries used in the inlet and outlet segments was about 30 μm. The optical pathlength between the optical fibers was about 4 mm. The capillaries and fibers were glued into the wafers using UV-activated optical cement. Each optical fiber extends into the central segment approximately 1000 μm and the annular spacing is approximately 2–3 μm. Optimally, for an optical fiber having a diameter of 110 μm, each optical fiber extends into the central segment 20 by a distance ranging from approximately 50–4000 μm from the centerline of either the inlet segment 16 or the outlet segment 18.

Although the present invention has been described in considerable detail with reference to certain preferred versions thereof, other versions are possible. For example, the angles between the central segment and the inlet and outlet segments can be approximately 20°, 80°, 50°, etc. Further, the materials for the substrate, the capillaries and the arms can be different than those specified herein without significantly affecting the performance of the device. Therefore, the spirit and scope of the appended claims should not be limited to the description of the preferred versions contained herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function should not be interpreted as a "means" or "step" clause as specified in 35 U.S.C. §112.

The invention claimed is:

1. A microfluidic detection device comprising:
 (a) a cell body which is composed of a ceramic material;
 (b) a flow path through the cell body, the flow path comprising:
  (i) an inlet segment having a first longitudinal axis;
  (ii) an outlet segment having a second longitudinal axis; and
  (iii) a central segment located between the inlet segment and the outlet segment and in fluid communication with both the inlet segment and the outlet segment, the central segment having an inner surface which is exposed to fluid flowing along the flow path and which is composed of the ceramic material;
  wherein the central segment has a first junction with the inlet segment and a second junction with the outlet segment and wherein the central segment has a third longitudinal axis, the third longitudinal axis being transverse to the first longitudinal axis and the second longitudinal axis;
 (c) a first optical fiber having a portion located in the first junction so that a first substantially annular region is formed between the first optical fiber and the inner surface of the central segment, wherein the first optical fiber has a diameter and the first annular region has a length that is approximately 1–40 times the diameter of the first optical fiber; and
 (d) a second optical fiber having a portion located in the second junction so that a second substantially annular region is formed between the second optical fiber and the inner surface of the central segment, wherein the second optical fiber has a diameter and the second annular region has a length that is approximately 1–40 times the diameter of the second optical fiber;
 wherein the portions of the optical fibers located in the junctions are situated so that fluid entering the central segment of the flow path flows through one of the annular regions and fluid exiting the central segment of the flow path flows through the other annular region.

2. The device of claim 1 wherein the length of the first annular region is approximately 4–10 times the diameter of the first optical fiber.

3. The device of claim 2 wherein the length of the second annular region is approximately 4–10 times the diameter of the second optical fiber.

4. The device of claim 1 wherein the distance between the inner surface of the central segment and the first optical fiber is approximately 0.001–0.2 times the diameter of the first optical fiber.

5. The device of claim 4 wherein the distance between the inner surface of the central segment and the second optical fiber is approximately 0.001–0.2 times the diameter of the second optical fiber.

6. The device of claim 4 wherein the distance between the inner surface of the central segment and the first optical fiber is approximately 0.01–0.05 times the diameter of the first optical fiber.

7. The device of claim 6 wherein the distance between the inner surface of the central segment and the second optical fiber is approximately 0.01–0.05 times the diameter of the second optical fiber.

8. The device of claim 1 further comprising:
 (e) a light source in optical communication with the first optical fiber; and
 (f) a light detector in optical communication with the second optical fiber.

9. The device of claim 1 wherein each of the optical fibers is substantially cylindrical.

10. The device of claim 1 wherein the third longitudinal axis is substantially perpendicular to both the first longitudinal axis and the second longitudinal axis.

11. The device of claim 1 wherein each of the inlet segment and the outlet segment has an inner diameter smaller than the inner diameter of the central segment.

12. The device of claim 1 wherein the ceramic material at the inner surface of the central segment is an etched ceramic material.

13. The device of claim 1 wherein the ceramic material at the inner surface of The central segment is etched silica.

14. The device of claim 1 wherein each of the first and second optical fibers has a substantially circular cross-section and an outer diameter, and the central segment comprises a conduit having a substantially circular cross-section having an inner diameter larger than the outer diameter of the optical fibers.

15. The device of claim 1 wherein
 (i) the inlet segment comprises an inlet capillary tube secured within an inlet conduit,
 (ii) the outlet segment comprises an outlet capillary tube secured within an outlet conduit, and
 (iii) the central segment comprises a central conduit;
 the inlet conduit, the outlet conduit and the central conduit having substantially the same substantially circular cross-section.

16. The device of claim 1 wherein the cell body comprises first and second ceramic wafers, each of the wafers including a mating surface having a pattern etched thereon, and the mating surfaces being bonded together so that the etched patterns together provide the flow path.

17. The device of claim 1 wherein
 (i) the inlet segment comprises an inlet capillary tube secured within an inlet conduit,
 (ii) the outlet segment comprises an outlet capillary tube secured within an outlet conduit, and
 (iii) the central segment comprises a central conduit;
 the inlet conduit, the outlet conduit and the central conduit having substantially the same substantially circular cross-section.

18. A microfluidic detection device comprising:
 (a) a cell body which is composed of a ceramic material;
 (b) a flow path in the cell body, the flow path comprising:
  (i) an inlet segment having a first longitudinal axis;
  (ii) an outlet segment having a second longitudinal axis; and
  (iii) a central segment located between the inlet segment and the outlet segment and in fluid communication with both the inlet segment and the outlet segment, the central segment having an inner surface which is exposed to fluid flowing along the flow path and which is composed of the ceramic material;

wherein the central segment has a first junction with the inlet segment and a second junction with the outlet segment and wherein the central segment has a third longitudinal axis, the third longitudinal axis being transverse to the first longitudinal axis and the second longitudinal axis;

(c) a first arm having a portion located in the first junction so that a first substantially annular region is formed between the first arm and the inner surface of the central segment, wherein the first arm has a diameter and the first annular region has a length that is approximately 1–40 times the diameter of the first arm; and (d) a second arm having a portion located in the second junction so that a second substantially annular region is formed between the second arm and the inner surface of the central segment, wherein the second arm has a diameter and the second annular region has a length that is approximately 1–40 times the diameter of the second arm;

wherein the portions of the arms located in the junctions are situated so that fluid entering the central segment of the flow path flows through one of the annular regions and fluid exiting the central segment of the flow path flows through the other annular region.

19. The device of claim 18 wherein
(i) the length of the first annular region is approximately 4–10 times the diameter of the first optical fiber; and
(ii) the length of the second annular region is approximately 4–10 times the diameter of the second optical fiber;
(iii) the distance between the inner surface of the central segment and the first optical fiber is approximately 0.01–0.05 times the diameter of the first optical fiber; and
(iv) the distance between the inner surface of the central segment and the second optical fiber is approximately 0.01–0.05 times the diameter of the second optical fiber.

20. The device of claim 18 wherein the cell body is transparent to wavelengths of light permitting measurements of fluorescence, degenerate four wave mixing, Raman, refractive index, or surface plasmon resonance to be taken through the cell body.

21. The device of claim 18 wherein the ceramic material at the inner surface of the central segment is etched silica.

22. The device of claim 18 wherein each of the first and second arms has a substantially circular cross-section and an outer diameter, and the central segment comprises a conduit having a substantially circular cross-section having an inner diameter larger than the outer diameter of the arms.

23. The device of claim 18 wherein the cell body comprises first and second ceramic wafers, each of the wafers including a mating surface having a pattern etched thereon, and the mating surfaces being bonded together so that the etched patterns together provide the flow path.

24. A microfluidic detection device comprising:
(1) a cell body which is composed of a ceramic material and which comprises first and second ceramic wafers, each of the wafers including a mating surface having a pattern etched thereon, the mating surfaces being bonded together so that the patterns together provide a flow path through the cell body, the flow path comprising:

(i) an inlet segment having a first longitudinal axis;
(ii) an outlet segment having a second longitudinal axis; and
(iii) a central segment which is located between the inlet segment and the outlet segment and in fluid communication with both the inlet segment and the outlet segment, the central segment having a substantially cylindrical inner surface which is exposed to fluid flowing along the flow path and which is composed of the ceramic material;

wherein the central segment has a first junction with the inlet segment and a second junction with the outlet segment and wherein the central segment has a third longitudinal axis, the third longitudinal axis being transverse to the first longitudinal axis and the second longitudinal axis;

a first substantially cylindrical optical fiber having a first diameter and having a portion located in the first junction so that a first substantially annular region is formed between the first optical fiber and the inner surface of the central segment, the first annular region having a length approximately 1–40 times the first diameter; and a second substantially cylindrical optical fiber having the first diameter and having a portion located in the second junction so that a second substantially annular region is formed between the second optical fiber and the inner surface of the central segment, the second annular region having a length approximately 1–40 times the first diameter;

wherein the portions of the optical fibers located in the junctions are situated so that fluid entering the central segment of the flow path flows through one of the annular regions, and fluid exiting the central segment of the flow path flows through the other annular region.

25. The device of claim 24 wherein
(i) the length of the first annular region is approximately 4–10 times the diameter of the first optical fiber; and
(ii) the length of the second annular region is approximately 4–10 times the diameter of the second optical fiber;
(iii) the distance between the inner surface of the central segment and the first optical fiber is approximately 0.01–0.05 times the diameter of the first optical fiber; and
(iv) the distance between the inner surface of the central segment and the second optical fiber is approximately 0.01–0.05 times the diameter of the second optical fiber.

26. The device of claim 24 wherein the ceramic material at the inner surface of the central segment is etched silica.

27. The device of claim 24 wherein
(i) the inlet segment comprises an inlet capillary tube secured within an inlet conduit,
(ii) the outlet segment comprises an outlet capillary tube secured within an outlet conduit, and
(iii) the central segment comprises a central conduit;
the inlet conduit, the outlet conduit and the central conduit having substantially the same substantially circular cross-section.

* * * * *